United States Patent [19]

Murayama

[11] 4,153,634
[45] May 8, 1979

[54] PROCESS FOR PREPARING METHYL HEPTENONE FROM PRENYL MESITYL OXIDE USING AN AMINE CATALYST

[75] Inventor: Stanley T. Murayama, Rocky Hill, N.J.

[73] Assignee: Rhodia, Inc., New York, N.Y.

[21] Appl. No.: 813,381

[22] Filed: Jul. 6, 1977

[51] Int. Cl.² .............................................. C07C 49/04
[52] U.S. Cl. ............................................... 260/593 R
[58] Field of Search ....................... 260/593 R, 593 E

[56] References Cited

U.S. PATENT DOCUMENTS

| | | | |
|---|---|---|---|
| 3,002,999 | 10/1961 | Lichtenberger et al. | 260/593 R |
| 3,668,255 | 6/1972 | Meuly | 260/593 R |
| 3,933,895 | 1/1976 | Nelson | 560/53 |
| 3,933,898 | 1/1976 | Nelson | 560/53 |
| 3,976,700 | 8/1976 | DeSimone | 260/593 R |

*Primary Examiner*—James O. Thomas, Jr.
*Assistant Examiner*—James H. Reamer

[57] ABSTRACT

A process is provided for preparing methyl heptenone from a ketone mixture comprising isomers of prenyl mesityl oxide; the mixture is subjected to hydrolytic cracking with water in the presence of an amine catalyst, and, optionally, an inorganic alkali, at an elevated temperature, and methyl heptenone is recovered.

34 Claims, No Drawings

PROCESS FOR PREPARING METHYL HEPTENONE FROM PRENYL MESITYL OXIDE USING AN AMINE CATALYST

U.S. Pat. No. 3,668.255, patented June 6, 1972 to Meuly and Gradeff, provides a process for the alkylation of aliphatic ketones having an alpha hydrogen, substitution occuring on the carbon alpha to the carbonyl group, by use of solid alkali in the presence of an organic amine and/or ammonia as a catalyst. The reaction products are alkenyl highly branched ketones having a pleasant odor, useful in the formulation of perfumes and perfume bases. Many of these ketones are prepared for the first time by this process.

The process is particularly useful for the preparation of methyl heptenone. If acetone is reacted with 1-chloro-3-methyl-2-butene, good yields of methyl heptenone are obtained. However, the methyl heptenone is accompanied by a higher boiling ketone fraction, that constitutes a considerable proportion of the reaction product. In Example 27 of the patent, for example, the yield included 86 grams of crude methyl heptenone and 42 grams of the higher ketone residue, and the crude methyl heptenone only comprised 72% methyl heptenone. Economic application of this process to the preparation of methyl heptenone clearly requires conversion of the higher boiling ketone fraction into a useful product.

Analysis of the higher boiling ketone fraction has shown that it is a mixture containing large amounts of isomeric ketones of the following structure:

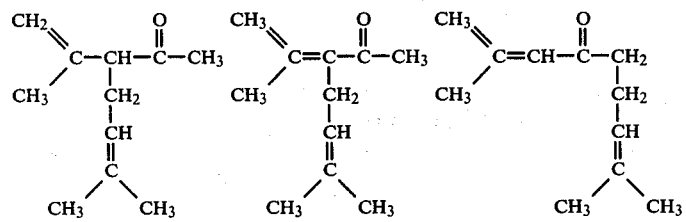

Acetone under the reaction conditions forms also some diacetone alcohol and mesityl oxide, and these then react with the prenyl chloride to produce the above isomers of prenyl mesityl oxide, also called prenyl-substituted methyl pentenones, in the same manner as acetone reacts with prenyl chloride to produce methyl heptenone. It is also possible that prenyl chloride reacts with the diacetone alcohol in the same manner to give the corresponding hydroxy derivatives that subsequently dehydrate. The presence of such hydroxy ketones is observed in the residues of the methyl heptenone production by the process of U.S. Pat. No. 3,668,255.

German Pat. No. 875,512 to Binapfl, published May 4, 1953, proposed the hydrolysis of unsaturated ketones having a carbonyl group in the vicinity of an ethylenically unsaturated group by heating in the presence of water with the addition of acid, particularly weak acid, such as boric acid, adipic acid and benzoic acid. Rupture of the ketone molecule follows addition of water at the ethylenic linkage, and the product is a mixture of ketones and aldehydes. The process is indicated as applicable to aromatic and cycloaliphatic ketones, such as 1-cyclohexylidene-cyclohexanone-2 and 1-oxy-1,3-diphenyl-2-butylene.

German Pat. No. 927,688 to Stichnoth, published May 16, 1955, suggested the conversion of o-cyclohexylidene-cyclohexanone to cyclohexanone, using water, in the presence of a small amount of alkali, at elevated temperatures.

German Pat. No. 946,443 to Wolf, published Feb. 2, 1956, proposed modification of the process of German Pat. No. 875,512 by the use of alkali rather than acid. As the alkali, alkali metal hydroxides such as potassium and sodium hydroxide, as well as alkali metal compounds such as their carbonates, was suggested, as well as alkaline earth metal hydroxides such as calcium hydroxide. The process was indicated as applicable to cycloaliphatic and aromatic ketones, such as 1-cyclohexenyl-cyclohexanone-2- and acetophenone.

In accordance with U.S. Pat. No. 3,976,700 to De Simone patented Aug. 24, 1976, the higher boiling ketone mixture of U.S. Pat. No. 3,668,255, containing prenyl-substituted methyl pentenones, is converted to methyl heptenone by hydrolytic cracking in the presence of alkali and water at a temperature within the range from about 50° to about 350° C. The resulting increased yield of methyl heptenone makes the production of methyl heptenone from acetone quite attractive commercially.

The process of U.S. Pat. No. 3,976,700 makes it possible to prepare methyl heptenone from mesityl oxide. Mesityl oxide is reacted with prenyl chloride at a temperature within the range from about −20° to about 150° C. in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the mesityl oxide and prenyl chloride being in the molar ratio of from about 1:5 to about 20:1, the alkali hydroxide being in the proportion of from about 1 to about 2 moles per mole of prenyl chloride, and the amount of nitrogen compound being within the range from about 0.003 mole to about 1 mole per mole of prenyl chloride; thereby forming and separating a prenyl-substituted methyl pentenone mixture. The ketone mixture is subjected to hydrolytic cracking with water in the presence of alkali at a temperature within the range from about 50° to about 350° C., forming methyl heptenone, which is recovered from the resulting reaction mixture.

The process as applied to mesityl oxide is thus carried out in two steps, with or without intermediate purification of the ketone mixture prior to hydrolytic cracking, in accordance with the following reaction scheme:

Step I:

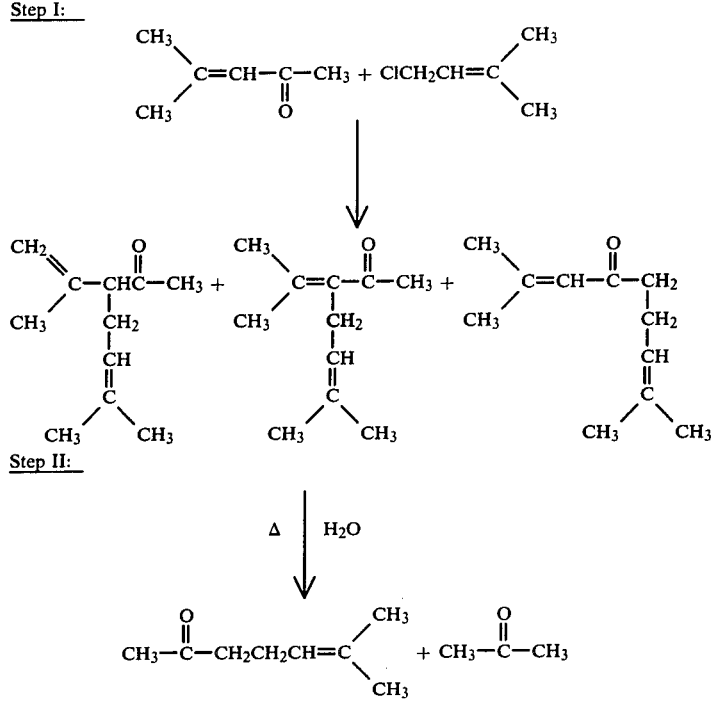

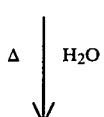

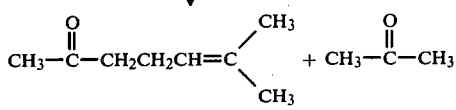

U.S. Pat. No. 3,976,700 also provides a process for preparing methyl heptenone from acetone. Acetone is reacted with prenyl chloride at a temperature within the range from about −20° to about 150° C. in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the acetone and prenyl chloride being in the molar ratio of from about 1:5 to about 20:1, the alkali hydroxide being in the proportion of from about 1 to about 2 moles per mole of prenyl chloride, and the amount of nitrogen compound being within the range from about 0.003 mole to about 1 mole per mole of prenyl chloride. Methyl heptenone is recovered from the reaction mixture, preferably by distillation. The residual ketonic mixture comprising prenyl-substituted methyl pentenones is then subjected to hydrolytic cracking with water in the presence of alkali at a temperature within the range from about 50° to about 350° C.; forming additional methyl heptenone, which is recovered from the hydrolytic reaction mixture.

The process when starting with acetone is thus carried out in two steps, with separation of methyl heptenone produced in the first step before hydrolytic cracking of the prenyl-substituted methyl pentenones that are obtained as a by-product in the first step, in accordance with the following reaction scheme:

Step I: (a)

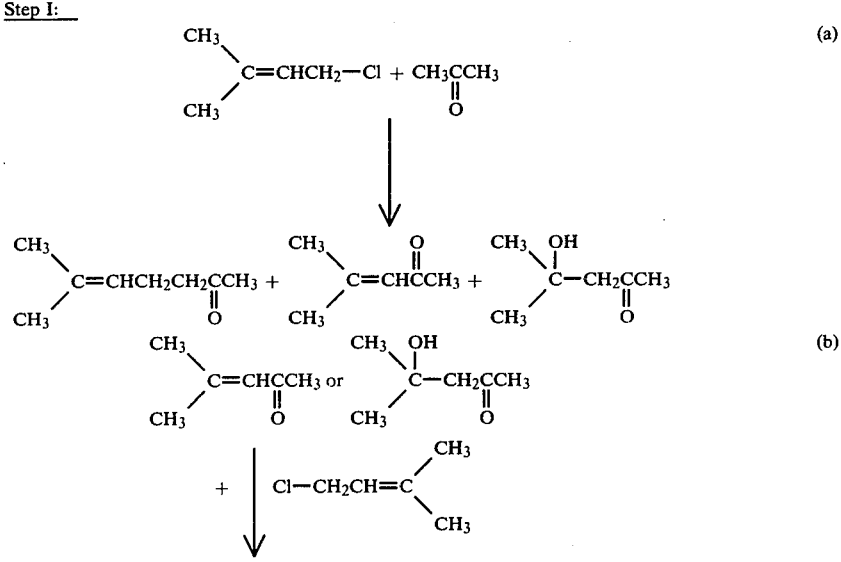

(b)

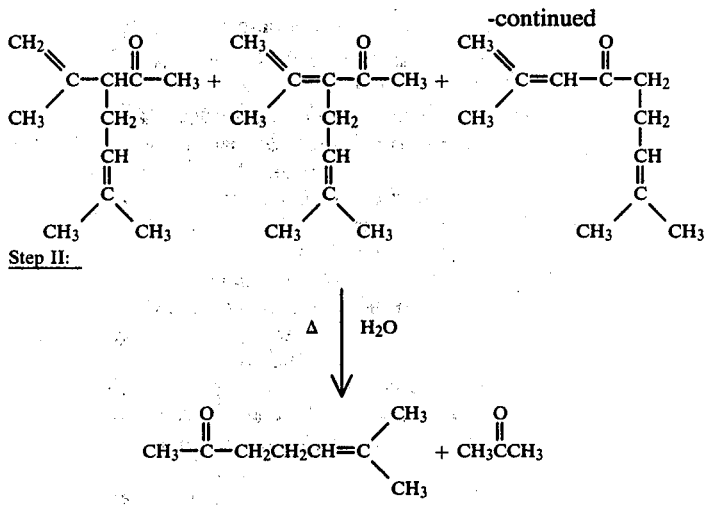

Step II:

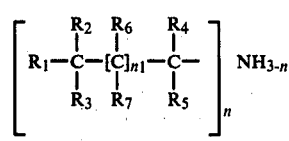

The hydrolytic cracking reaction of Step II with water and alkali is preferably carried out at elevated temperatures, and in a pressure vessel. The reaction can be conducted over a wide temperature range, within the range from about 50° to about 350° C., and preferably within the range from about 230° to about 310° C.

U.S. Pat. No. 3,976,700 also discloses that addition of acetone or other low-boiling aliphatic ketone otherwise stable under the reaction conditions increases the reaction rate considerably, and permits completion of the cracking in a very short time, ranging from about one minute to about one hour. The aliphatic ketones useful for this purpose for this purpose contain from about three to about ten carbon atoms, in a straight or branched chain. The patent further states that the same effect on the reaction rate is exerted by lower aliphatic alcohols such as methanol, ethanol, isopropanol, butanol, isobutanol, amyl and isoamyl alcohol, as well as prenyl alcohol. No explanation is offered for the enhanced rate, which appears to be a solvent effect.

In accordance with the instant invention, a process is provided for preparing methyl heptenone from a ketone mixture comprising prenyl-substituted methyl pentenones, which comprises subjecting the ketone mixture to hydrolytic cracking in the presence of an amine catalyst, water, and optionally an inorganic alkali, at a temperature within the range from about 10° to about 350° C., and recovering methyl heptenone from the hydrolytic reaction mixture.

The amine catalyst has at least two functional groups, of which at least one group is an amine group and the other group can be another amine group, a hydroxyl group or an alkoxy group.

The class of amine catalysts useful in the process in accordance with the invention is defined by the following formula:

$$[R-(A-Z)_m]_n NH_{3-n} \qquad I$$

in which
m is a number from 1 to 10;
n is 1, 2 or 3;
Z is an aliphatic-hydrocarbon, phenylene, cycloaliphatic-hydrocarbon, aliphatic-phenylene or aliphatic-cycloaliphatic radical having from one to about twenty carbon atoms;
A is selected from the group consisting of —NH and O; and
R is selected from the group consisting of hydrogen, alkyl having from one to about six carbon atoms, —R'NH$_2$ or —R'OH, where R'=alkylene having from one to about six carbon atoms.

In the case where A is NH and R is H, the compounds have the formula:

$$[NH_2-Z]_n-NH_{3-n} \qquad II$$

In the case where A is NH and R is alkyl, the compounds have the formula:

$$[RNH-Z]_n-NH_{3-n} \qquad III$$

In the case where A is O and R is H, the compounds have the formula:

$$[HO-Z]_n-NH_{3-n} \qquad IV$$

In the case where A is O and R is alkyl, the compounds have the formula:

$$[RO-Z]_n-NH_{3-n} \qquad V$$

In the formulae II, III, IV and V,
n is 1, 2 or 3; and
In formulae III and V,
R is alkyl.

A particularly preferred class of compounds has the formula:

$$\left[ R_1-\underset{\underset{R_3}{|}}{\overset{\overset{R_2}{|}}{C}}-[C]_{n_1}-\underset{\underset{R_5}{|}}{\overset{\overset{R_4}{|}}{C}}- \right]_n NH_{3-n} \qquad VI$$

wherein
R$_1$ is selected from the group consisting of amino, hydroxyl, and alkoxy groups;
R$_2$, R$_3$, R$_4$, R$_5$, R$_6$, and R$_7$ are selected from the group consisting of hydrogen H, hydroxyl OH, amino NH$_2$, alkoxy, alkyl, hydroxyalkyl and amino-alkyl groups having from one to about six carbon atoms;
n is 1, 2 or 3; and
n$_1$ is a number from 0 to about 10, preferably from 0 to 3.

When R$_1$ is NH$_2$ and n is 1, the compounds have the formula:

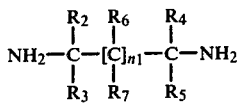

(1)

When R₁ is OH the compounds have the formula:

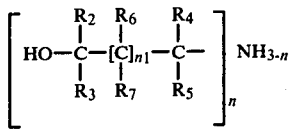

(2)

When R₁ is alkoxy and n is 1, compounds have the formula:

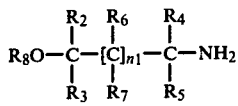

(3)

wherein
$R_2$, $R_3$, $R_4$, $R_5$, $R_6$, $R_7$ and $n_1$ are as defined above in connection with Formula VI, and $R_8$ is lower alkyl having from one to five carbon atoms.

These amine catalysts considerably increase the rate of reaction and, therefore, reduce the total reaction time, at the same time considerably increasing the yield that is obtainable within a given reaction time, as compared to a reaction system that does not contain the amine catalyst under otherwise identical reaction conditions.

Moreover, the amine catalyst makes unnecessary the addition of inorganic alkali. However, inorganic alkali can be used if desired, and if used may further increase the yield obtainable under otherwise similar reaction conditions.

Exemplary Z radicals, when Z is aliphatic, include straight chain and branched chain alkylene groups, which optionally may contain unsaturated groups, such as ethylenic $>C\!=\!C<$ and acetylenic $-C\!\equiv\!C-$ linkages, and have from two to about twenty carbon atoms. Exemplary Z alkylene groups include ethylene, propylene, butylene, pentylene, hexylene, heptylene, octylene, nonylene, decylene, undecylene, dodecylene, 2,2-dimethyl-propylene, 2-methyl-2-ethyl propylene, 2,2,4-trimethyl-butylene, 2,4-dimethyl-butylene, 2,4-dimethyl-pentylene, 2-methyl-propylene, 2,2-diethyl-propylene, 2,3-dimethyl-butylene, 2,3-diethyl-butylene, 2,3,4-trimethyl pentylene.

Exemplary cycloaliphatic Z radicals include cyclopentylene, cyclohexylene, cyclobutylene, cycloheptylene, cyclooctylene and cyclodecylene.

When Z is cycloalkylene or phenylene, the functional amino, hydroxyl or alkoxyl group is attached to the ring by way of an alkylene group having from one to about six carbon atoms, preferably methylene or ethylene.

Exemplary R alkyl radicals include methyl, ethyl, propyl, isopropyl, butyl, isobutyl, sec-butyl, tert-butyl, amyl, isoamyl, sec-amyl, tert-amyl, neopentyl, hexyl, isohexyl, sec-hexyl, tert-hexyl, 1,2-dimethyl butyl and neohexyl.

Exemplary R' alkylene radicals include methylene, ethylene, propylene, butylene, amylene, neopentylene, hexylene and neohexylene.

Exemplary polyamines falling within the above classes include ethylene diamine, propylene diamine, butylene diamine, pentylene diamine (pentamethylene diamine), hexylene diamine (hexamethylene diamine) octylene diamine, decylene diamine and dodecylene diamine. Exemplary aminoalcohols falling within the above classes include monoethanolamine, diethanolamine, triethanolamine, propanolamine, butanolamine, dibutanolamine, dipropanolamine, tripropanolamine, tributanolamine, pentanolamine, hexanolamine, heptanolamine, octanolamine, nonanolamine, decanolamine, and dodecanolamine.

Exemplary aminoethers include methoxyethylamine, ethoxyethylamine, propoxyethylamine, butoxyethylamine, butoxybutylamine, propoxypropylamine, and ethoxyethyleneoxyethylamines.

While the amine catalyst apparently serves the function of an inorganic alkali, as the hydrolytic cracking of U.S. Pat. No. 3,976,700, an inorganic alkali hydroxide can be added, and when it is added, the reaction rate may be further increased, and the yield further enhanced.

As the inorganic alkali, there can be used an alkali metal hydroxide, such as sodium hydroxide and potassium hydroxide, and any alkaline earth metal hydroxide, such as calcium hydroxide, strontium hydroxide and barium hydroxide. Also useful are alkaline-reacting salts, such as the alkali metal and alkaline earth metal carbonates, bicarbonates, borates, tartrates, oxalates, acetates, formates and sulfites, for example, sodium carbonate, sodium bicarbonate, potassium carbonate, and potassium bicarbonate.

The reaction may be conducted over a wide temperature range, within the range from about 10° to about 350° C. Since however good yields are obtained at low reaction temperatures, within the range from about 75 to about 150° C., the preferred reaction temperatures are within that range.

The reaction proceeds at atmospheric pressure, but when reaction temperatures are employed at above the boiling point of volatile ingredients in the reaction system, the reaction can be carried out under a condenser, or in a pressure vessel, such as an autoclave. When the autoclave is used, high pressures may be developed without disadvantage, up to an including 100 psi. Preferably, however, the reaction is carried out under a condenser or fractionating column at atmospheric pressure.

The reaction time depends to some extent upon the reaction temperature, the reactants, and the amine catalyst. The reaction proceeds well with good yields at reaction times that are normally less than four hours, and frequently less than two hours, but in some cases a longer reaction time may be required, up to eight to twelve hours.

If an inorganic alkali is employed, the alkali concentration in the aqueous phase of the reaction system is important. The alkali concentration in this phase should be within the range from about 2 to about 60% and preferably from about 6 to about 50%. Water is of course required in the course of the hydrolytic cracking, and forms a separate phase with the prenyl-substituted methyl pentenone mixture. The two phases are brought into contact during the reaction by stirring, or other conventional mixing technique.

The amine catalyst undergoes partition between the aqueous and organic ketone phases. Consequently, the proportion of amine catalyst to aqueous alkali is also important, to ensure an adequate concentration of amine in both the aqueous and the organic phases. The ratio of amine catalyst: aqueous alkali (i.e. the aqueous alkaline phase, having a base concentration within the range from about 2 to about 60%) is within the range from 1:1.1 to 1:3, and perferably within the range from 1:0.3 to 1.1.

The amount of prenyl mesityl oxide that can be hydrolytically cleaved by feeding it to a given mass of catalyst consisting of water-alkali-amine is theoretically unlimited provided that water is supplied in order to compensate for the water used in the reaction and provided that the products of the reaction, methyl heptenone and acetone, are continuously withdrawn. Thus the process is ideally suited for a continuous mode of operation.

The process can also be carried out in a batchwise manner whereby the amount of ketone vis-à-vis catalyst could be either very small or so high as to be stoichiometrically equivalent to the amount of water present in the system. Of course larger amounts of ketone could be added to the batch, but this will be of no advantage.

The following Examples in the opinion of the inventors represent preferred embodiments of the invention.

EXAMPLES 1 to 29

These examples illustrate the process of the invention using a variety of amine catalysts, with and without inorganic alkali. The prenyl mesityl oxide used as a starting material was prepared in accordance with the following procedure:

To a well-stirred mixture of 278 g (6.75 mol, 97.2% assay) of sodium hydroxide beads, 1477 g (15 mols, 98% assay) of mesityl oxide and 538 g (5 mols, 97.5% assay) of 1-chloro-3-methyl-2-butene is added 6.5 g of 40% aqueous dimethylamine. The exothermic reaction raises the temperature to 45° C. over a ten minute period. For the next 125 minutes a cooling bath is used as needed to maintain the reaction temperature between 45° C. and 50° C. The reaction is cooled to 30° C. and 1000 g of water is added with stirring to dissolve the inorganic salts. The organic layer is separated, washed with 500 g of water and distilled to give, after removal of mesityl oxide, 863 g of crude prenyl mesityl oxide isomers (PMO): bp 60°–100° C. (2 Torr), 78% assay. Fractionation of the crude PMO through a 15-plate Goodloe column affords PMO of 98.9% purity: bp 70°–83° C. (3 Torr).

In each of Examples 1 to 29, a small portion of this material was cleaved hydrolytically by the following procedure:

20 g of prenyl mesilyl oxide, i.e., 0.118 mole, 98.9%, was combined with 8 g of the amine catalyst indicated in Table I, either no alkali or alkali in the amount indicated in Table I, and the amount of water indicated in Table I, in a reaction vessel fitted with a thermometer, stirrer, short Vigreux column, and a distilling head. The reaction mixture in each Example was heated to the temperature given over two hours. The prenyl mesityl oxide was thereby cleaved to methyl heptenone and acetone, and the extent of the reaction determined in terms of the percent of prenyl mesityl oxide (% PMO) reacted, by a determination by vapor phase chromatography of the amount of residual prenyl mesityl oxide in the reaction vessel at the conclusion of the reaction.

The results obtained are shown in Table I.

TABLE I

| Example No. | Amine catalyst | Base | g | Water (g) | Temp °C. | % PMO reacted |
|---|---|---|---|---|---|---|
| | ALKANOLAMINES | | | | | |
| 1 | Ethanolamine | NaOH | 2 | 2 | 25[1] | 73.7 |
| 2 | Ethanolamine | None | — | 3 | 115 | 41.4 |
| 3 | Ethanolamine | Na$_2$HPO$_4$ | 1 | 3 | 116 | 49.0 |
| 4 | Ethanolamine | Na$_2$B$_4$O$_4$ | 1 | 3 | 113 | 43.4 |
| 5 | Ethanolamine | K$_2$CO$_3$ | 1 | 3 | 117 | 92.4 |
| 6 | Ethanolamine | NaAcetate | 1 | 3 | 127 | 64.6 |
| 7 | Ethanolamine | KHCO$_3$ | 1 | 3 | 125 | 63.1 |
| 8 | Ethanolamine | LiOH | 1 | 3 | 112 | 96.0 |
| 9 | Ethanolamine | Ba(OH)$_2$ | 1 | 3 | 111 | 88.9 |
| 10 | Ethanolamine | KOH | 1 | 3 | 119 | 99.0 |
| 11 | Ethanolamine | NaOH | 1 | 3 | 118 | 99.0 |
| 12 | Ethanolamine | Quat. base[2] | 1 | 3 | 109 | 99.0 |
| 13 | Ethanolamine | NaOH | 2 | 3 | 136 | 100 |
| 14 | Ethanolamine | NaOH | 0.5 | 3.5 | 116 | 99.0 |
| 15 | Ethanolamine | NaOH | 0.5 | 7.5 | 110 | 97.5 |
| 16 | Ethanolamine[3] | NaOH | 0.5 | 3.5 | 112 | 69.7 |
| 17 | Diethanolamine | NaOH | 2 | 2 | 134 | 29.8 |
| 18 | Triethanolamine | NaOH | 2 | 2 | 133 | 34.3 |
| 19 | Triethanolamine | NaOH | 4 | 4 | 133 | 57.1 |
| 20 | 2-Amino-2-ethyl-1,3-propane-diol | NaOH | 2 | 2 | 127 | 53.0 |
| | POLYAMINES | | | | | |
| 21 | Ethylene diamine | NaOH | 2 | 2 | 120 | 85.9 |
| 22 | Ethylene diamine | NaOH | 0.5 | 3.5 | 112 | 79.3 |
| 23 | Ethylene diamine | None | — | 3 | 109 | 30.3 |
| 24 | 1,3-Propylene-diamine | NaOH | 2 | 2 | 132 | 72.7 |
| 25 | 1,6-Diamino-hexane | NaOH | 2 | 2 | 130 | 60.0 |
| 26 | 1,8-Diamino-octane | NaOH | 2 | 2 | 130 | 55.0 |
| 27 | 1,12-Diamino-dodecane | NaOH | 2 | 2 | 130 | 50.0 |
| | ALKOXYALKYLAMINES | | | | | |
| 28 | 2-Methoxyethyl-amine | NaOH | 2 | 2 | 108 | 27.2 |
| 29 | 2-Ethoxyethyl- | NaOH | 2 | 2 | 115 | 35.0 |

TABLE I-continued

| Example No. | Amine catalyst | Base | g | Water (g) | Temp °C. | % PMO reacted |
|---|---|---|---|---|---|---|
| | aine | | | | | |

[1] Reaction time 96 hours
[2] Tetramethyl ammonium hydroxide
[3] 4 g ethanolamine The above results are to be contrasted with the results for Example 13 of U.S. Pat. No. 3,976,700, which, for convenience of reference, is duplicated below:

Into a 1-liter stainless steel reaction vessel equipped with a distillation line and vapor recovery condenser were charged:

| Prenyl mesityl oxide | 100 g |
|---|---|
| Water and sodium hydroxide as 30% aqueous sodium hydroxide | 140 g |

The reaction was carried out at 140° C. at atmospheric pressure, distilling off acetone as it was formed. Samples were taken during the reaction, and analyzed by vapor phase chromatography for prenyl mesityl oxide (PMO) and methyl heptenone (MH). The reaction log was as follows:

| Time Total Minutes | Temp ° C. | Sample II | PMO | NH |
|---|---|---|---|---|
| 0 | 30 | | | |
| 240 | 90 | 1 | 92.5 | 0 |
| 480 | 140 | 2 | 81.6 | 7.4 |
| 720 | 140 | 3 | 70.2 | 13.3 |
| 960 | 140 | 4 | 60.0 | 18.2 |

After cooling, the reaction vessel was discharged, rinsed with acetone and the two layers separated after salting the organic layer with 50.0 g sodium chloride. The aqueous layer was then extracted with benzene. The combined organic layer and benzene extracts were distilled at 28 mm vacuum after removal of the benzene.

A total of 97 g organics was recovered. Analysis of the combined fractions indicated 15.0 methyl heptenone (0.126 mole). The direct yield was 20.0% and the true yield 50.0%.

It is apparent from these results that the process of the invention gives a considerably improved yield, in a far shorter reaction time.

U.S. Pat. No. 3,976,700 indicates that the reaction time shown can be decreased by incorporating lower aliphatic alcohol in the reaction mixture. However, a lower aliphatic alcohol, although effective, is not as effective as the amine catalysts of the instant invention, as the following comparison shows:

The reaction procedure of Examples 1 to 29 was duplicated, substituting alcohol for the amine catalyst. The following results were obtained:

| Example No. | Amine Catalyst | g | Base | g | Water (g) | Temp °C. | % PMO reacted |
|---|---|---|---|---|---|---|---|
| Control A | Pentanol | 8 | NaOH | 2 | 2 | 128 | 42.4 |
| Control B | Cyclohexanol | 8 | NaOH | 2 | 2 | 128 | 29.3 |
| Control C | 2-ethylhexanol | 8 | NaOH | 2 | 2 | 137 | 20.2 |

EXAMPLE 30

In this Example, the hydrolytic cleavage was carried out continuously. In a heated reactor were placed a catalytic system composed of 8 g ethanol-amine, 1 g potassium carbonate, and 3 g of water. The reactor was heated to 114° C. Prenyl mesityl oxide was then added to the reactor at a rate of about 10 g/hour. At the same time, steam at a temperature of 120° C. was admitted into the reactor at a rate of 30 g/hour. Reaction began at once, and methyl heptenone was steam-distilled out of the reaction system, together with acetone. The acetone and methyl heptenone were separated in a fractioning column.

Having regard to the foregoing disclosure, the following is claimed as the inventive and patentable embodiments thereof:

1. A process for preparing methyl heptenone from a ketone mixture comprising prenyl-substituted methyl pentenones, which comprises subjecting the ketone mixture to hydrolytic cracking with water in the presence of an aqueous solution of an amine catalyst having at least two functional groups of which at least one group is an amine group and the other group is selected from the group consisting of another amine group, a hydroxyl group and an alkoxy group, and having the formula:

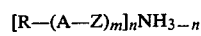

$[R-(A-Z)_m]_n NH_{3-n}$ in which
m is a number from 1 to 10;
n is 1, 2 or 3;
Z is selected from the group consisting of aliphatic hydrocarbon, phenylene, cycloaliphatic hydrocarbon, aliphatic hydrocarbon-phenylene and aliphatic-cycloaliphatic hydrocarbon radicals having from one to about twenty carbon atoms;
A is selected from the group consisting of —NH and O; and
R is selected from the group consisting of hydrogen, alkyl having from one to about six carbon atoms, —R'NH$_2$ and —R'OH, where R' is alkylene having from one to about six carbon atoms
at a temperature within the range from about 10° to about 350° C., and recovering methyl heptenone from the hydrolytic reaction mixture.

2. A process according to claim 1 in which
m is 1;
n is 1;
Z is, aliphatic hydrocarbon;
A is selected from the group consisting —NH and O; and
R is selected from the group consisting of hydrogen, alkyl having from one to about six carbon atoms, —R'NH$_2$ and —R'OH, where R' is alkylene having from one to about six carbon atoms.

3. A process according to claim 1, in which R is hydrogen and A is NH.

4. A process according to claim 1, in which R is alkyl and A is NH.

5. A process according to claim 1, in which R is hydrogen and A is —O—.

6. A process according to claim 1, in which R is alkyl and A is —O—.

7. A process according to claim 1, in which the amine catalyst has the formula:

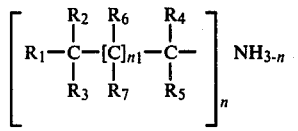

wherein
$R_1$ is selected from the group consisting of amino, hydroxyl, and alkoxy groups;
$R_2$, $R_3$, $R_4$, $R_5$, $R_6$ and $R_7$ are selected from the group consisting of hydrogen H, hydroxyl OH, amino $NH_2$, alkoxy, alkyl, hydroxyalkyl and amino-alkyl groups having from one to about six carbon atoms;
n is 1, 2 or 3; and
$n_1$ is a number from 0 to about 10.

8. A process according to claim 7, in which $R_1$ is $NH_2$ and n is 1.

9. A process according to claim 8, in which $R_2$, $R_3$, $R_4$ and $R_5$ are H and $n_1$ is 0.

10. A process according to claim 7, in which $R_1$ is OH and n is 1.

11. A process according to claim 10, in which $R_2$, $R_3$, $R_4$, $R_5$ are H and $n_1$ is 0.

12. A process according to claim 11, in which $R_2$, $R_3$, $R_4$, $R_5$ are H, $n_1$ is 0, and R' is methyl or ethyl.

13. A process according to claim 7, in which $R_1$ is OH and n is 2.

14. A process according to claim 7, in which $R_1$ is OH and n is 3.

15. A process according to claim 1, in which an inorganic alkali is also present in the hydrolytic cracking.

16. A process according to claim 15, in which the hydrolytic cracking is carried out in a reaction system including an aqueous phase and the alkali concentration in the aqueous phase is within the range from about 2 to about 60%.

17. A process according to claim 16, in which the ratio of amine catalyst: the aqueous alkaline is within the range from 1:0.1 to 1:3.

18. A process according to claim 17, in which the aqueous phase has a base concentration within the range from about 2 to about 60%.

19. A process according to claim 1, in which the reaction temperature is within the range from about 75° to about 150° C.

20. A process according to claim 1, in which the hydrolytic cracking is carried out at atmospheric pressure.

21. A process according to claim 1, in which the hydrolytic cracking is carried out at an elevated pressure up to 1000 psi.

22. A process according to claim 15, in which the inorganic alkali is an alkali metal or alkaline earth metal hydroxide.

23. A process according to claim 15, in which the inorganic alkali is an alkaline alkali metal or alkaline earth metal salt.

24. A process according to claim 1, in which methyl heptenone and acetone are separated together from the hydrolytic cracking reaction as the reaction proceeds.

25. A process according to claim 1, in which the prenyl-substituted methyl pentenones are added continuously to a reaction system composed of amine catalyst and any aqueous alkali, with a concomitant addition of water to supply that consumed in the course of the reaction.

26. A process according to claim 25, in which the water is added as steam, and methyl heptenone and acetone steam-distilled out of the hydrolytic cracking reaction as the reaction proceeds.

27. In the process for preparing methyl heptenone from acetone which comprises reacting acetone at a temperature within the range from about —20° to about 150° C. with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro-substituents; the amounts of the acetone and prenyl chloride being in the molar ratio of from about 1.5 to about 20:1, the alkali metal hydroxide being in the proportion of from about 1 to about 2 moles per mole of prenyl chloride, and the amount of nitrogen compound being within the range from about 0.003 mole to about 1 mole per mole of prenyl chloride, the improvement which comprises separating methyl heptenone from the reaction mixture comprising prenyl-substituted methyl pentenones; subjecting the prenyl-substituted methyl pentenones to hydrolytic cracking with water in the presence of an amine catalyst having at least two functional groups, of which at least one group is an amine group and the other group is selected from the group consisting of another amine group, a hydroxyl group and an alkoxy group, and having the formula:

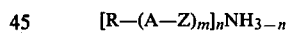

in which
m is a number from 1 to 10;
n is 1, 2 or 3;
Z is selected from the group consisting of aliphatic hydrocarbon, phenylene, cycloaliphatic hydrocarbon, aliphatic hydrocarbon-phenylene and aliphatic-cycloaliphatic hydrocarbon radicals having from one to about twenty carbon atoms;
A is selected from the group consisting of —NH and O; and
R is selected from the group consisting of hydrogen, alkyl having from one to about six carbon atoms, —R'$NH_2$ and —R'OH, where R' is alkylene having from one to about six carbon atoms,
at a temperature within the range from about 10° to about 350° C., and recovering additional methyl heptenone from the resulting reaction mixture, thereby improving the overall yield of methyl heptenone from acetone.

28. A process according to claim 27, in which the hydrolytic cracking is carried out in the presence of inorganic alkali.

29. A process in accordance with claim 27, in which a mixture of mesityl oxide and acetone is reacted with the prenyl chloride.

30. In the process for preparing methyl heptenone from mesityl oxide which comprises reacting mesityl oxide at a temperature within the range from about $-20°$ to about $150°$ C. with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents; the amounts of the mesityl oxide and prenyl chloride being in the molar ratio of from about 1:5 to about 20:1, the alkali metal hydroxide being in the proportion of from about 1 to about 2 moles per mole of prenyl chloride, and the amount of nitrogen compound being within the range from about 0.003 mole to about 1 mole per mole of prenyl chloride; the improvement which comprises separating from the reaction mixture a fraction comprising prenyl-substituted methyl pentenones; subjecting the prenyl-substituted methyl pentenone fraction to hydrolytic cracking with water in the presence of an amine having at least two functional groups, of which at least one group is an amine group and the other group is selected from the group consisting of another amine group, a hydroxyl group and an alkoxyl group, and having the formula:

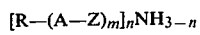

in which
m is a number from 1 to 10;
n is 1, 2 or 3;
Z is selected from the group consisting of aliphatic hydrocarbon, phenylene, cycloaliphatic hydrocarbon, aliphatic hydrocarbon-phenylene and aliphatic-cycloaliphatic hydrocarbon radicals having from one to about twenty carbon atoms;
A is selected from the group consisting of —NH and O; and
R is selected from the group consisting of hydrogen, alkyl having from one to about six carbon atoms, —R'NH$_2$ and —R'OH, where R' is alkylene having from one to about six carbon atoms, at a temperature within the range from about $10°$ to about $350°$ C.; and recovering methyl heptenone from the resulting reaction mixture, thereby improving the overall yield of methyl heptenone from mesityl oxide.

31. A process according to claim 30, in which the hydrolytic cracking is carried out in the presence of inorganic alkali.

32. A process according to claim 1, in which the amine catalyst has the formula:

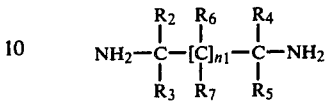

wherein
R$_2$, R$_3$, R$_4$, R$_5$, R$_6$ and R$_7$ are selected from the group consisting of hydrogen H, Hydroxyl OH, amino NH$_2$, alkoxy, alkyl, hydroxyalkyl and amino-alkyl groups having from one to about six carbon atoms; and
n$_1$ is a number from 0 to about 10.

33. A process according to claim 1, in which the amine catalyst has the formula:

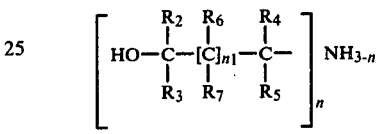

wherein
R$_2$, R$_3$, R$_4$, R$_5$, R$_6$ and R$_7$ are selected from the group consisting of hydrogen H, hydroxyl OH, amino NH$_2$, alkoxy, alkyl, hydroxyalkyl and amino-alkyl groups having from one to about six carbon atoms;
n is 1, 2 or 3; and
n$_1$ is a number from 0 to about 10.

34. A process according to claim 1, in which the amine catalyst has the formula:

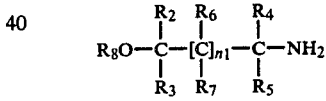

wherein
R$_2$, R$_3$, R$_4$, R$_5$, R$_6$, and R$_7$ are selected from the group consisting of hydrogen H, hydroxyl OH, amino NH$_2$, alkoxy, alkyl, hydroxyalkyl and aminoalkoxyl groups having from one to about six carbon atoms;
n$_1$ is a number from 0 to about 10; and
R$_8$ is lower alkyl having from one to five carbon atoms.

* * * * *

UNITED STATES PATENT AND TRADEMARK OFFICE
CERTIFICATE OF CORRECTION

PATENT NO. : 4,153,634
DATED : May 8, 1979
INVENTOR(S) : Stanley T. Murayama

It is certified that error appears in the above-identified patent and that said Letters Patent are hereby corrected as shown below:

Column 1, line 9 : "occuring" should be --occurring--
Column 1, line 32:

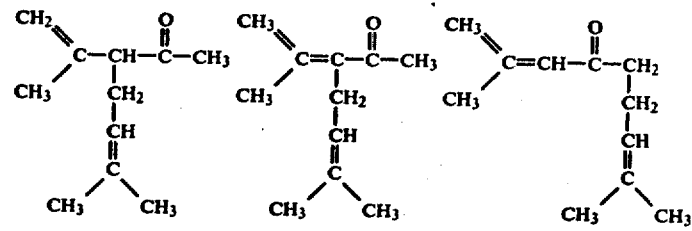

should be

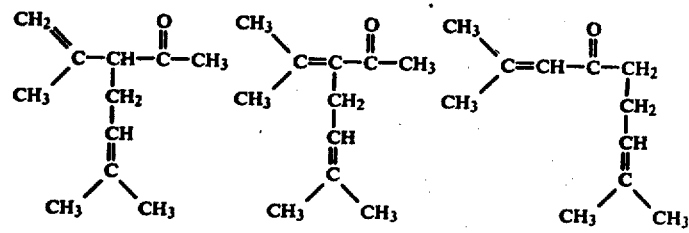

UNITED STATES PATENT AND TRADEMARK OFFICE
CERTIFICATE OF CORRECTION

PATENT NO. : 4,153,634

DATED : May 8, 1979

INVENTOR(S) : Stanley T. Murayama

It is certified that error appears in the above-identified patent and that said Letters Patent are hereby corrected as shown below:

Column 4, formula (b) :

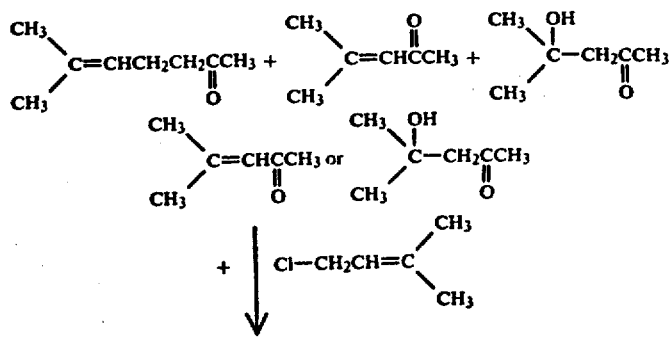

should be

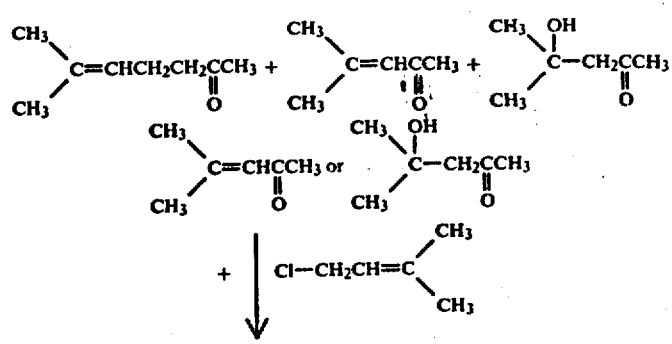

UNITED STATES PATENT AND TRADEMARK OFFICE
CERTIFICATE OF CORRECTION

PATENT NO. : 4,153,634

DATED : May 8, 1979

INVENTOR(S) : Stanley T. Murayama

It is certified that error appears in the above-identified patent and that said Letters Patent are hereby corrected as shown below:

Column 5, line 1 :

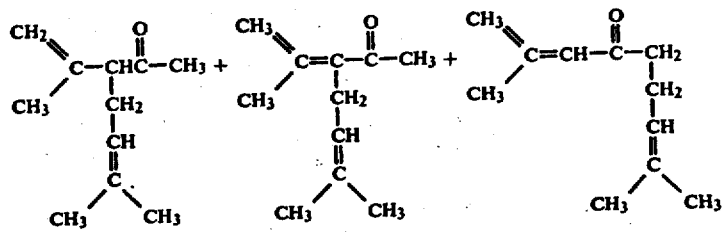

should be

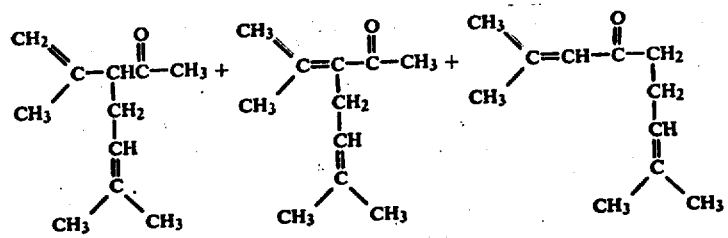

Column 6, lines 50-55:

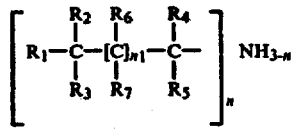

should be

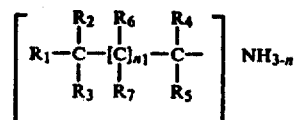

UNITED STATES PATENT AND TRADEMARK OFFICE
CERTIFICATE OF CORRECTION

PATENT NO. : 4,153,634
DATED : May 8, 1979
INVENTOR(S) : Stanley T. Murayama

It is certified that error appears in the above-identified patent and that said Letters Patent are hereby corrected as shown below:

Column 7, line 10 :

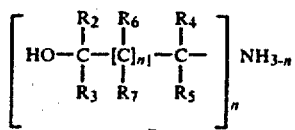

should be

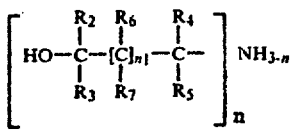

| | |
|---|---|
| Column 9, line 4 : | "1:1.1" should be --1:0.1-- |
| Column 9, line 4 : | "perferably" should be --preferably-- |
| Column 10, line 11: | "60°-100°C" should be --60°-110°C.-- |
| Column 10, line 68: | "2-ethoxyethyl" should be --2-ethoxyethyl-amine- |
| Column 11, line 4: | delete "aine" |
| Column 11, line 30: | "NH" should be --MH-- |
| Column 12, line 61: | after "consisting" please add --of-- |
| Column 13, line 15: | |

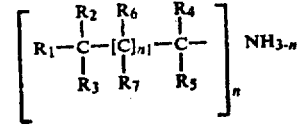

should be

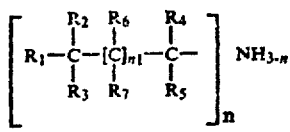

UNITED STATES PATENT AND TRADEMARK OFFICE
CERTIFICATE OF CORRECTION

PATENT NO. : 4,153,634
DATED : May 8, 1979
INVENTOR(S) : Stanley T. Murayama

It is certified that error appears in the above-identified patent and that said Letters Patent are hereby corrected as shown below:

Column 13, line 34 : "11" should be --10--.
Column 13, line 48 : "alkaline" should be --alkali--.

Signed and Sealed this

Twenty-second Day of January 1980

[SEAL]

Attest:

SIDNEY A. DIAMOND

*Attesting Officer*    *Commissioner of Patents and Trademarks*